United States Patent
Clarke et al.

(10) Patent No.: US 7,211,688 B2
(45) Date of Patent: May 1, 2007

(54) PROCESS FOR THE PRODUCTION OF AN ALKENYL CARBOXYLATE OR AN ALKYL CARBOXYLATE

(75) Inventors: Robert William Clarke, Driffield (GB); Robert Croll, Edinburgh (GB); Andrew Richard Lucy, Brough (GB); Bruce Leo Williams, Brough (GB)

(73) Assignee: BP Chemicals Limited, Middlesex (GB)

( * ) Notice: Subject to any disclaimer, the term of this patent is extended or adjusted under 35 U.S.C. 154(b) by 191 days.

(21) Appl. No.: 10/505,660

(22) PCT Filed: Feb. 12, 2003

(86) PCT No.: PCT/GB03/00619

§ 371 (c)(1),
(2), (4) Date: Aug. 25, 2004

(87) PCT Pub. No.: WO03/074465

PCT Pub. Date: Sep. 12, 2003

(65) Prior Publication Data

US 2005/0085659 A1    Apr. 21, 2005

(30) Foreign Application Priority Data

Mar. 4, 2002  (GB) .................. 0205014.4

(51) Int. Cl.
C07C 67/05   (2006.01)
C07C 69/02   (2006.01)
C07C 67/02   (2006.01)
C07C 51/16   (2006.01)

(52) U.S. Cl. .................. 560/243; 560/231; 560/261; 562/548

(58) Field of Classification Search .......... 560/243, 560/231, 261; 562/548
See application file for complete search history.

(56) References Cited

U.S. PATENT DOCUMENTS 5,300,682 A * 4/1994 Blum et al. ............ 562/512.2
5,304,678 A * 4/1994 Lemanski et al. ......... 562/548
6,040,474 A * 3/2000 Jobson et al. ............ 560/243
6,147,273 A   11/2000 Stickney et al.

FOREIGN PATENT DOCUMENTS

EP    0 985 657 A1   3/2000
WO    WO 98/05620    2/1998

OTHER PUBLICATIONS

Mason, Kenneth; "Chemical Process" *Research Disclosure*; Publications, Hampshire, GB, No. 338 (1992) pp. 445-447; XP 000315650.

* cited by examiner

*Primary Examiner*—Samuel A Barts
*Assistant Examiner*—Lalitha Nagubandi
(74) *Attorney, Agent, or Firm*—Nixon & Vanderhye

(57) ABSTRACT

Process for producing an alkyl carboxylate, comprising contacting in an oxidation reaction zone a $C_2$ to $C_4$ alkane, a molecular oxygen-containing gas, the corresponding alkene and optionally water, in the presence of at least one catalyst active for the oxidation of the alkane to the corresponding alkene and carboxylic acid, to produce a first product stream comprising alkene, unreacted alkane, carboxylic acid and water; separating in a first separation means at least a portion of the product stream produced in the oxidation reaction zone into a gaseous stream comprising alkene and unreacted alkane and a liquid stream comprising carboxylic acid and water; and separating by chemical treatment at least a portion of the gaseous stream obtained from the first separation means into respective streams rich in alkene and alkane; wherein the chemical treatment comprises the steps of: (1) contacting the alkene/alkane gaseous stream with a solution of a metal salt capable of selectively chemically absorbing the alkene to produce a chemically absorbed alkene-rich liquid stream, and (2) recovering an alkene rich stream from the metal salt solution. In a second reaction zone, at least a portion of the alkene rich stream obtained from the second separation means and a corresponding carboxylic acid are contacted, in the presence of at least one catalyst active for the production of alkyl carboxylate, to produce a second product stream comprising alkyl carboxylate.

36 Claims, 1 Drawing Sheet

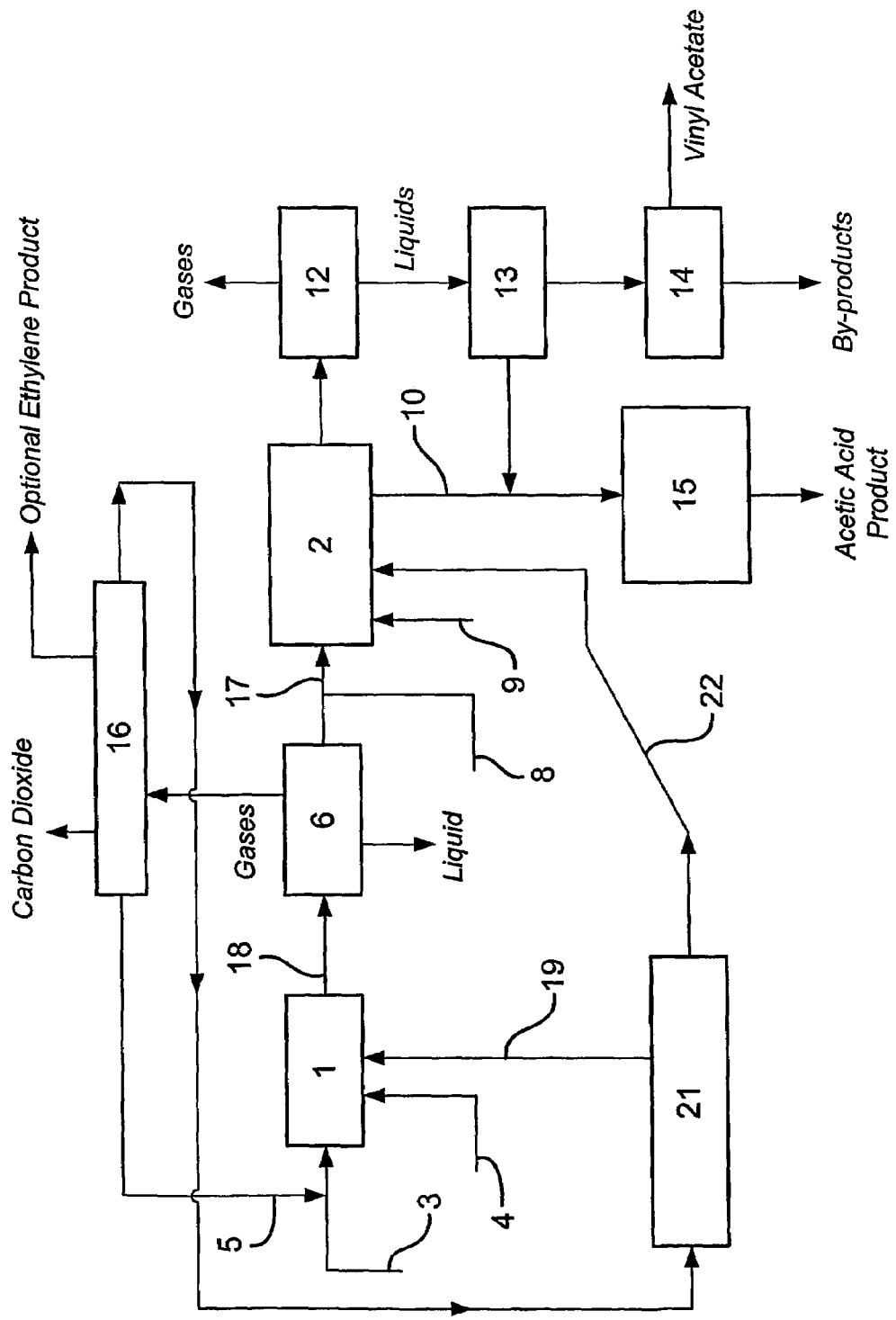

PROCESS FOR THE PRODUCTION OF AN ALKENYL CARBOXYLATE OR AN ALKYL CARBOXYLATE

This application is the U.S. National Phase of International Application PCT/GB03/00619, filed 12 Feb. 2003, which designated the U.S. PCT/GB03/00619 claims priority to British Application No. 0205014.4 filed 4 Mar. 2002. The entire content of these applications are incorporated herein by reference.

The present invention relates to an integrated process for the oxidation of a $C_2$ to $C_4$ alkane to produce the corresponding alkene and carboxylic acid and wherein the alkene and carboxylic acid are further used as reactants to produce an alkenyl carboxylate alkyl carboxylate.

BACKGROUND OF THE INVENTION

Carboxylic acids are useful feedstocks for the production of alkenyl carboxylates and alkyl carboxylates. Thus, for example, acetic acid is used to manufacture vinyl acetate or ethyl acetate. Acetic acid may be produced by the catalytic oxidation of ethylene and/or ethane.

Vinyl acetate is generally prepared commercially by contacting ethylene and acetic acid with molecular oxygen in the presence of a catalyst active for the production of vinyl acetate. Ethyl acetate is generally prepared by contacting ethylene and acetic acid in the presence of a catalyst active for the production of ethyl acetate.

Integrated processes for producing acetic acid and/or vinyl acetate are known in the art. EP-A-0 877 727 discloses an integrated process for the production of acetic acid and/or vinyl acetate from a gaseous feedstock comprising ethylene and/or ethane. The integrated process comprises a first step wherein ethylene and/or ethane is catalytically oxidised in a first reaction zone to produce a product stream comprising ethylene, unreacted ethane, acetic acid and water. This product stream may be passed directly to a second reaction zone and contacted therein with a molecular oxygen-containing gas in the presence of a suitable catalyst to produce vinyl acetate.

Research Disclosure 2244 of 1992 (June) No. 338 describes a process for the oxidation of ethane and/or ethylene to produce acetic acid in which the by-product carbon monoxide is oxidised to carbon dioxide. According to this document, the unreacted ethane and/or ethylene may be recycled to the oxidation reactor. Alternatively, the ethylene may be reacted with acetic acid to produce ethyl acetate or with acetic acid and oxygen to form vinyl acetate.

In the manufacture of vinyl acetate or ethyl acetate from ethylene and acetic acid, the molar ratio of the ethylene to acetic acid is desirably unity or approximately unity. Thus, in an integrated process in which ethane is oxidised to produce ethylene and acetic acid, the molar ratio of ethylene to acetic acid produced in the oxidation reaction is also desirably unity or approximately unity.

In the partial oxidation of a gaseous feedstock comprising ethylene and ethane, the product stream generally comprises ethylene, unreacted ethane, acetic acid and water. This product stream may be condensed and/or scrubbed to produce a gaseous stream comprising ethylene and ethane and a liquid stream comprising acetic acid and water. The gaseous stream comprising ethylene is typically recycled to the oxidation reactor. Continuous recycling of such an ethylene-containing stream will result in a build-up of ethylene in the oxidation reactor. As the concentration of ethylene increases the oxidation catalyst will become more selective towards acetic acid and the carbon oxides thereby deviating from the desired ethylene to acetic acid molar ratio of unity or approximately unity.

SUMMARY OF THE INVENTION

Thus there remains a need for an improved integrated process for the manufacture of an alkenyl carboxylate such as vinyl acetate or alkyl carboxylate such as ethyl acetate.

In particular, it would be desirable, if in an integrated process for the production of an alkenyl carboxylate by the oxidation of a $C_2$ to $C_4$ alkane to produce the corresponding alkene and carboxylic acid and wherein the alkene and carboxylic acid are contacted with a molecular oxygen-containing gas to produce the alkenyl carboxylate, to be able to optimise the amount of alkene fed to the alkane oxidation reaction zone such that an equimolar or approximate equimolar ratio of acid to alkene may be achieved, such as 0.8:1 to 1.4:1 and to also optimise the amount of alkene fed to the alkenyl carboxylate reaction zone such that high selectivity to vinyl acetate may be achieved.

Accordingly, in a first embodiment, the present invention provides an integrated process for the production of an alkenyl carboxylate which process comprises the steps:
(a) contacting in an oxidation reaction zone a $C_2$ to $C_4$ alkane, a molecular oxygen-containing gas, the corresponding alkene and optionally water, in the presence of at least one catalyst active for the oxidation of the alkane to the corresponding alkene and carboxylic acid, to produce a first product stream comprising alkene, unreacted alkane, carboxylic acid and water;
(b) separating in a first separation means at least a portion of the product stream produced in the oxidation reaction zone into a gaseous stream comprising alkene and unreacted alkane and a liquid stream comprising carboxylic acid and water;
(c) separating in a second separation means at least a portion of the gaseous stream obtained from the first separation means into respective streams rich in alkene and alkane;
(d) contacting in a second reaction zone at least a portion of said alkene rich stream obtained from the second separation means, a corresponding carboxylic acid and a molecular oxygen-containing gas, in the presence of at least one catalyst active for the production of alkenyl carboxylate to produce a second product stream comprising alkenyl carboxylate.

In a second embodiment, the present invention provides an integrated process for the production of an alkyl carboxylate which process comprises the steps:
(a) contacting in an oxidation reaction zone a $C_2$ to $C_4$ alkane, a molecular oxygen-containing gas, the corresponding alkene and optionally water, in the presence of at least one catalyst active for the oxidation of the alkane to the corresponding alkene and carboxylic acid, to produce a first product stream comprising alkene, unreacted alkane, carboxylic acid and water;
(b) separating in a first separation means at least a portion of the product stream produced in the oxidation reaction zone into a gaseous stream comprising alkene and unreacted alkane and a liquid stream comprising carboxylic acid and water;
(c) separating in a second separation means at least a portion of the gaseous stream obtained from the first separation means into respective streams rich in alkene and alkane;
(d) contacting in a second reaction zone at least a portion of said alkene rich stream obtained from the second separation means and a corresponding carboxylic acid, in the presence of at least one catalyst active for the production of alkyl carboxylate to produce a second product stream comprising alkyl carboxylate.

Advantageously, the process of the present invention, allows an optimal amount of alkene to be fed to each of the two reaction zones thereby improving overall process efficiency.

Each of the alkane, molecular oxygen-containing gas, alkene and water may be introduced into the oxidation reaction zone as fresh feed and/or recycle component.

In the present invention, preferably, the C2 to C4 alkane is ethane, the corresponding alkene being ethylene and the corresponding carboxylic acid being acetic acid. In the first embodiment of the present invention, the ethylene and acetic acid are reacted with a molecular oxygen-containing gas to produce vinyl acetate.

In the second embodiment of the present invention the ethylene and acetic acid are reacted to produce ethyl acetate.

Typically, the oxidation reaction is performed heterogeneously with solid catalysts and the reactants in the fluid phase. In this case, the concentrations of alkene and optional water may be controlled as partial pressures in the oxidation reaction zone.

Catalysts active for the oxidation of alkane to alkene and carboxylic acid may comprise any suitable catalysts known in the art, for example, for the oxidation of ethane to ethylene and acetic acid as described in U.S. Pat. No. 4,596,787, EP-A-0407091, DE 19620542, WO 99/20592, DE 19630832, WO 98/47850, WO 99/51339, EP-A-0 1043064, WO 9913980, U.S. Pat. No. 5,300,682 and U.S. Pat. No. 5,300,684, the contents of which are hereby incorporated by reference.

U.S. Pat. No. 4,596,787 relates to a process for the low temperature oxydehydrogenation of ethane to ethylene using a catalyst having the empirical formula $Mo_aV_bNb_cSb_dX_e$ as therein defined, the elements being present in combination with oxygen.

EP-A-0407091 relates to process and catalyst for the production of ethylene and/or acetic acid by oxidation of ethane and/or ethylene in the presence of an oxidation catalyst comprising molybdenum, rhenium and tungsten.

DE 19620542 relates to molybdenum, palladium, rhenium based oxidation catalysts for the production of acetic acid from ethane and/or ethylene.

WO 99/20592 relates to a method of selectively producing acetic acid from ethane, ethylene or mixtures thereof and oxygen at high temperature in the presence of a catalyst having the formula $Mo_aPd_bX_cY_d$ wherein X represents one or several of Cr, Mn, Nb, Ta, Ti, V, Te and W; Y represents one or several of B, Al, Ga, In, Pt, Zn, Cd, Bi, Ce, Co, Rh, Ir, Cu, Ag, Au, Fe, Ru, Os, K, Rb, Cs, Mg, Ca, Sr, Ba, Nb, Zr, Hf, Ni, P, Pb, Sb, Si, Sn, Tl and U and a=1, b=0.0001 to 0.01, c=0.4 to 1 and d=0.005 to 1.

German patent application DE 196 30 832 A1 relates to a similar catalyst composition in which a=1, b>0, c>0 and d=0 to 2. Preferably, a=1, b=0.0001 to 0.5, c=0.1 to 1.0 and d=0 to 1.0.

WO 98/47850 relates to a process for producing acetic acid from ethane, ethylene or mixtures thereof and a catalyst having the formula $W_aX_bY_cZ_d$ in which X represents one or several of Pd, Pt, Ag and Au, Y represents one or several of V, Nb, Cr, Mn, Fe, Sn, Sb, Cu, Zn, U, Ni, and Bi and Z represents one or several of Li, Na, K, Rb, Cs, Be, Mg, Ca, Sr, Ba, Sc, Y, La, Tl, Zr, Hf, Ru, Os, Co, Rh, Ir, B, Al, Ga, In, Tl, Si, Ge, Pb, P, As and Te, a=1, b>0, c>0 and d is 0 to 2.

WO 99/51339 relates to a catalyst composition for the selective oxidation of ethane and/or ethylene to acetic acid which composition comprises in combination with oxygen the elements $Mo_aW_bAg_cIr_dX_eY_f$ wherein X is the elements Nb and V; Y is one or more elements selected from the group consisting of Cr, Mn, Ta, Ti, B, Al, Ga, In, Pt, Zn, Cd, Bi, Ce, Co, Rh, Cu, Au, Fe, Ru, Os, K, Rb, Cs, Mg, Ca, Sr, Ba, Zr, Hf, Ni, P, Pb, Sb, Si, Sn, Tl, U, Re and Pd; a, b, c, d, e and f represent the gram atom ratios of the elements such that $0<a\leq1$, $0\leq b<1$ and $a+b=1$; $0<(c+d)\leq0.1$; $0<e\leq2$; and $0\leq f\leq2$.

EP-A-1043064 relates to a catalyst composition for the oxidation of ethane to ethylene and/or acetic acid and/or for the oxidation of ethylene to acetic acid which composition comprises in combination with oxygen the elements molybdenum, vanadium, niobium and gold in the absence of palladium according to the empirical formula: $Mo_aW_bAu_cV_dNb_eY_f$ wherein Y is one or more elements selected from the group consisting of: Cr, Mn, Ta, Ti, B, Al, Ga, In, Pt, Zn, Cd, Bi, Ce, Co, Rh, Ir, Cu, Ag, Fe, Ru, Os, K, Rb, Cs, Mg, Ca, Sr, Ba, Zr, Hf, Ni, P, Pb, Sb, Si, Sn, Tl, U, Re, Te and La; a, b, c, d, e and f represent the gram atom ratios of the elements such that: $0<a\leq1$; $0\leq b<1$ and $a+b=1$; $10^{-5}<c\leq0.02$; $0<d\leq2$; $0<e\leq1$; and $0\leq f\leq2$.

WO 99/13980 relates to a catalyst for the selective oxidation of ethane to acetic acid of formula: $Mo_aV_bNb_cX_d$ wherein X is at least one promoter element selected from the group consisting of P, B, Hf, Te and As; a is a number ranging from about 1 to about 5; b is 1; c is a number ranging from about 0.01 to about 0.5; and d is a number ranging from greater than 0 to about 0.1.

U.S. Pat. No. 5,300,682 relates to the use of oxidation catalyst with empirical formula of $VP_aM_bO_x$ where M is one or more of Co, Cu, Re, Fe, Ni, Nb, Cr, W, U, Ta, Ti, Zr, Hf, Mn, Pt, Pd, Sn, Sb, Bi, Ce, As, Ag and Au, a is 0.5 to 3, b is 0 1 and x satisfies the valence requirements.

U.S. Pat. No. 5,300,684 relates to a fluid bed oxidation reaction using for example $Mo_{0.37}Re_{0.25}V_{0.26}Nb_{0.07}Sb_{0.03}Ca_{0.02}O_x$.

Other suitable oxidation catalysts for use in the present invention are described in WO 99/13980 which relates to the use of catalysts with elements in combination with oxygen in the relative gram atom ratios of $Mo_aV_bNb_cX_d$ where X=P, B, Hf, Te or As; U.S. Pat. No. 6,030,920 which relates to the use of catalysts with elements in combination with oxygen in the relative gram atom ratios of $Mo_aV_bNb_cPd_d$; WO 00/00284 which relates to the use of catalysts with elements in combination with oxygen in the relative gram atom ratios of $Mo_aV_bNb_cPd_d$ and/or $Mo_aV_bLa_cPd_d$; U.S. Pat. No. 6,087,297 which rela of catalysts with elements in combination with oxygen in the relative gram atom ratios of $Mo_aV_bPd_cLa_d$; WO 00/09260 which relates to the use of catalysts with elements in combination with oxygen in the relative gram atom ratios of $Mo_aV_bLa_cPd_dNb_eX_f$ where X=Cu or Cr and e and f can be zero; WO 00/29106 and WO 00/29105 which relate to the use of catalysts with elements in combination with oxygen in the relative gram atom ratios Of $Mo_aV_bGa_cPd_dNb_eX_f$ wherein X=La, Te, Ge, Zn, Si, In or W and WO 00/38833 which relates to the use of catalysts with elements in combination with oxygen in the relative gram atom ratios of $Mo_aV_bLa_cPd_dNb_eX_f$ wherein X=Al, Ga, Ge or Si, the contents of which are hereby incorporated by reference.

Solid catalysts active for the oxidation of the $C_2$ to $C_4$ alkane may be supported or unsupported. Examples of suitable supports include silica, diatomaceous earth, montmorillonite, alumina, silica alumina, zirconia, titania, silicon carbide, activated carbon and mixtures thereof.

Solid catalysts active for the oxidation of the $C_2$ to $C_4$ alkane may be used in the form of a fixed or fluidised bed.

The oxidation catalyst would be expected to oxidise at least part of any alkene fed to the oxidation reaction zone, for example to the corresponding carboxylic acid.

The molecular oxygen-containing gas used in the oxidation reaction zone, may be air or a gas richer or poorer in molecular oxygen than air. A suitable gas may be, for example, oxygen diluted with a suitable diluent, for example nitrogen or carbon dioxide. Preferably, the molecular oxygen-containing gas is oxygen. Preferably, at least some of the molecular oxygen-containing gas is fed to the oxidation reaction zone independently from the alkane and optional alkene feeds, and any recycle streams.

The alkane and alkene fed into the oxidation reaction zone of the process of the present invention may be substantially pure or may be admixed, for example, with one or more of nitrogen, argon, methane, carbon dioxide, carbon monoxide, hydrogen, and low levels of $C_3/C_4$ alkenes/alkanes.

Suitably, the concentration of alkene (as fresh feed and/or recycle component) is from greater than 0 and up to and including 50 mol % of the total feed, including recycles, to the oxidation reaction zone, preferably from 1 to 20 mol %, more preferably from 1 to 15 mol %.

Suitably, the concentration of water (as fresh feed and/or recycle component) is from 0 to 50 mol % inclusive of the total feed, including recycles, to the oxidation reaction zone, preferably from 0 to 25 mol %.

In one embodiment of the present invention, the alkene, such as ethylene, and water are co-fed into the oxidation reaction zone.

Suitably, the alkene, for example, ethylene, and water may be used in a ratio of 1:0.1–250 by weight, such as 1:0.1–100 or 1:0.1–50 but preferably in a ratio 1:0.1–10 by weight.

When solid catalysts are used in the oxidation reaction zone, the alkane, corresponding alkene, molecular-oxygen containing gas, optional water and any recycle gases are preferably passed through the oxidation reaction zone with a residence time corresponding to a combined gas hourly space velocity (GHSV) of 500–10,000 $hr^{-1}$; the GHSV being defined as volume (calculated at STP) of gas passing through the reactor divided by the bulk volume of settled catalyst.

The oxidation reaction of the present invention may suitably be carried out at a temperature in the range from 100 to 400° C., typically in the range 140 to 350° C.

The oxidation reaction of the present invention may suitably be carried out at atmospheric or superatmospheric pressure, for example, in the range from 5 to 27 barg.

Typically, alkane conversions in the range 1 to 99% may be achieved in the oxidation reaction of the present invention.

Typically, oxygen conversions in the range 30 to 100% may be achieved in the oxidation reaction of the present invention.

In the oxidation reaction of the present invention, the catalyst suitably has a productivity in the range 10 to 10000 grams of carboxylic acid, such as acetic acid, per hour per kilogram of catalyst.

In the oxidation reaction, the catalyst suitably has a productivity in the range 5 to 5000 grams of alkene, such as ethylene, per hour per kilogram of catalyst.

Carbon monoxide can have an adverse effect on some catalysts used in the production of vinyl acetate. Thus, depending on the nature of the catalyst employed, it is desirable, especially in the first embodiment of the present invention, that the first product stream should have a low concentration of carbon monoxide by-product, Thus, especially in the first embodiment of the present invention, it is also preferred to use a catalyst in the oxidation reaction zone that gives negligible carbon monoxide by-product. An additional catalyst component in the oxidation reaction zone may be used to oxidise carbon monoxide to carbon dioxide. The additional catalyst component may be present in the oxidation catalyst or catalysts or in a secondary reaction zone or may be present as a separate catalyst in the oxidation reaction zone.

When ethane is used as a reactant for the oxidation process, the product stream comprises acetic acid, ethylene and water, and may also contain ethane and oxygen, inert gas components such as argon and nitrogen and the by-products, acetaldehyde, carbon monoxide and carbon dioxide. Acetaldehyde and carbon monoxide may be converted by the molecular oxygen-containing gas to produce acetic acid and carbon dioxide respectively, either in downstream processes or, after recycling, in the oxidation reaction zone.

Ethylene is present in the product stream of the oxidation reaction as unconverted reactant ethylene from the feed and/or as oxidation product of the ethane reactant.

The product stream from the oxidation reaction zone is separated in a first separation means into a gaseous stream comprising the alkene and unreacted alkane and a liquid stream comprising the carboxylic acid. Any suitable separation means known in the art may be employed such as membrane separation, condensation or distillation. Preferably, the separation is carried out by condensation.

Where the product stream from the oxidation process comprises acetic acid, ethylene, ethane and water, the product stream may be, and is preferably, separated by condensation into an overhead gaseous stream comprising ethylene and ethane and a base liquid stream comprising acetic acid and water. In general, the gaseous stream will also comprise carbon oxides and oxygen.

Optionally, carboxylic acid and/or alkene may be recovered from the product stream of the oxidation process.

At least a portion of the gaseous stream from the first separation means is fed to a second separation means for separation into an alkene-rich stream and an alkane-rich stream. Any suitable means for separating alkenes from alkanes may be employed as the second separation means. Suitable means include cryogenic distillation, chemical treatment, membrane separation or pressure swing adsorption, preferably chemical treatment.

Chemical treatment may comprise the steps of (1) contacting the alkene/alkane gaseous stream with a solution of a metal salt capable of selectively chemically absorbing the alkene to produce a chemically absorbed alkene-rich liquid stream and (2) recovering an alkene rich stream from the metal salt solution.

Suitable metal salts are those capable of forming a complex with the alkene. Where, the alkene is ethylene, suitable metal salts comprise, chromium, copper (I), manganese, nickel, iron, mercury, silver, gold, platinum, palladium, rhodium, ruthenium, osmium, molybdenum, tungsten and rhenium.

Preferably, the metal salt comprises silver or copper (I), most preferably silver.

Where the metal salt is a silver salt, the silver salt is preferably, silver nitrate or silver fluoroborate.

Where the metal salt is a copper (I) salt, the copper (I) salt is preferably copper (I) acetate, copper (I) nitrate or copper (I) sulphate, most preferably copper (I) nitrate.

The metal solution may be aqueous or may comprise an organic nitrogen-containing compound such as pyridine.

The contacting of the gaseous stream with the metal salt solution may be carried out in any suitable means such as in an absorber column. The absorber column may be fitted with trays or packing such as raschig rings or structured packing. Preferably, the absorber column is fitted with packing.

To improve the purity of the alkene, the absorber column may suitably be equipped with a reboiler.

Preferably, the absorber column is operated with countercurrent flow of gas and metallic salt solution.

Suitably, the contacting may be carried out at a temperature in the range from −10 to 300° C., preferably 0 to 100° C. and at a pressure in the range from 1 to 70 barg, preferably 3 to 30 barg.

Where the contacting is carried out in an absorber column, the metal salt solution comprising the metal salt/alkene complex may be removed from the base of the absorber.

The alkane does not to any significant extent complex with the metal salt solution and may be removed as an overhead alkane-rich stream from the absorber column.

An alkene-rich stream may be recovered from the metal salt solution by heat, reduced pressure or by a combination thereof. Preferably, the solution is subjected to a reduced pressure such that the metal salt/alkene complex decomposes to release the alkene. The pressure reduction may be carried out in one or more stages, for example, in one or more flashing apparatus.

Where one or more flashing apparatus are employed, the alkene-rich stream is removed therefrom as an overhead stream. The overhead stream may be compressed prior to being optionally dried. Alternatively, the overhead stream may be dried prior to being compressed. Where the alkene-rich stream is compressed, it may be compressed to a pressure suitable for feeding to the second reaction zone. Suitably, it may be compressed to the pressure of any additional alkene feed to the second reaction zone.

The alkene-rich stream obtained from the second separation means will comprise the alkene and may comprise low levels of alkane and other impurities such as oxygen and carbon oxides.

Suitably, the alkene-rich stream, such as an ethylene-rich stream, obtained from the second separation means comprises at least 50% alkene, such as at least 80% alkene.

Preferably, the alkene-rich stream comprises at least 90% alkene, more preferably, 95% alkene, and most preferably, at least 99% alkene.

The alkene-rich stream may be recovered from the metal salt solution in one or more absorption/desorption stages, such as one absorption and two desorption stages.

Advantageously, the use of an alkene feed to the second reaction zone having reduced levels of impurities allows the amount of purge gas which has to be vented from the second reaction zone to be reduced and hence the loss of alkene from the second reaction zone is also reduced.

The alkane-rich stream obtained from the second separation means will comprise the alkane and may comprise low levels of alkene and other impurities such as oxygen and carbon dioxide.

Optionally, prior to contacting the alkene/alkane gaseous stream with the metal salt solution, the gaseous stream may be treated to remove components such as carbon dioxide, oxygen and oxygenates such as acetaldehyde.

The alkane-rich stream obtained from the second separation means may be fed as one or more streams to the oxidation reaction zone together with additional alkane.

The additional alkane may be fresh alkane and/or may be unreacted alkane from the oxidation reaction zone which has been recycled after the first separation means to the oxidation reaction zone.

The alkane stream from the second separation means and additional alkane may be introduced into the oxidation reaction zone either as separate feed streams or as a single feed stream comprising both the alkane from the second separation means and additional alkane.

In the first, preferred, embodiment of the present invention, the alkene-rich stream is fed as one or more streams, to a second reaction zone together with additional molecular oxygen-containing gas, optional additional alkene and carboxylic acid to produce alkenyl carboxylate, such as vinyl acetate.

In the second embodiment of the present invention, the alkene-rich stream is fed as one or more streams, to a second reaction zone together with optional additional alkene and carboxylic acid to produce alkyl carboxylate, such as ethyl acetate.

The alkene from the second separation means and additional alkene may be introduced into the second reaction zone either as separate feed streams or as a single feed stream comprising both alkene from the second separation means and additional alkene.

The additional alkene may be fresh alkene and/or recycled alkene from the second reaction zone and/or a portion of the alkane/alkene stream from the oxidation reaction zone.

Additional alkene introduced into the second reaction zone for the production of alkenyl carboxylate or alkyl carboxylate may be substantially pure or may be admixed, for example, with one or more of nitrogen, argon, methane, carbon dioxide, carbon monoxide, hydrogen, and low levels of $C_3/C_4$ alkenes/alkanes.

Advantageously, the process of the first embodiment of the present invention allows optimal process efficiency to be achieved by using high concentrations of alkene to be fed to the second reaction zone and low concentrations of alkene to be fed to the oxidation reaction zone. Low concentrations (less than 20 mol % of total feed) of alkene fed to the oxidation reaction zone allow the required equimolar or approximate equimolar mixture of alkene and carboxylic acid to be produced. High concentrations of alkene (greater than 50 mol % of the total feed) fed to the second reaction zone maximize the selectivity to alkenyl carboxylate product such as vinyl acetate.

Similarly, the process of the second embodiment of the present invention allows optimal process efficiency to be achieved by using optimal concentrations of alkene to be fed to the second reaction zone and low concentrations of alkene to be fed to the oxidation reaction zone. Low concentrations (less than 20 mol % of total feed) of alkene fed to the oxidation reaction zone allow the required equimolar or approximate equimolar mixture of alkene and carboxylic acid to be produced. Optimal concentrations of alkene may be fed to the second reaction zone to maximize the selectivity to alkyl carboxylate product such as ethyl acetate.

Desirably, the concentration of alkene (optional additional alkene feed and alkene obtained from the second separation means), such as ethylene, fed to the second reaction zone is at least 50 mol % of the total feed to the second reaction zone, preferably, at least 55 mol %, more preferably at least 60 mol %. Suitably, the concentration of alkene is up to 85 mol % of the total feed to the second reaction zone, preferably, in the range at least 50 mol % to 80 mol %, such as at least 55 mol % to 80 mol %.

Catalysts known in the art for the production of alkenyl carboxylates may be used in the first embodiment of the process of the present invention. Thus, catalyst active for the production of vinyl acetate which may be used in a second reaction zone of the present invention may comprise, for example, catalysts as described in GB 1 559 540; U.S. Pat. No. 5,185,308 and EP-A-0672453 the contents of which are hereby incorporated by reference.

GB 1 559 540 describes a catalyst active for the preparation of vinyl acetate by the reaction of ethylene, acetic acid and oxygen, the catalyst consisting essentially of: (1) a catalyst support having a particle diameter of from 3 to 7 mm and a pore volume of from 0.2 to 1.5 ml/g, a 10% by weight water suspension of the catalyst support having a pH from 3.0 to 9.0, (2) a palladium-gold alloy distributed in a surface layer of the catalyst support, the surface layer extending less than 0.5 mm from the surface of the support, the palladium in the alloy being present in an amount of from 1.5 to 5.0 grams per litre of catalyst, and the gold being present in an amount of from 0.5 to 2.25 grams per litre of catalyst, and (3) from 5 to 60 grams per litre of catalyst of alkali metal acetate.

U.S. Pat. No. 5,185,308 describes a shell impregnated catalyst active for the production of vinyl acetate from ethylene, acetic acid and an oxygen containing gas, the catalyst consisting essentially of: (1) a catalyst support having a particle diameter from about 3 to about 7 mm and a pore volume of 0.2 to 1.5 ml per gram, (2) palladium and gold distributed in the outermost 1.0 mm thick layer of the catalyst support particles, and (3) from about 3.5 to about 9.5% by weight of potassium acetate wherein the gold to palladium weight ratio in said catalyst is in the range 0.6 to 1.25.

EP-A-0672453 describes palladium containing catalysts and their preparation for fluid bed vinyl acetate processes.

Typically, the production of alkenyl carboxylate such as vinyl acetate in the second reaction zone is carried out heterogeneously with the reactants being present in the gas phase.

The molecular oxygen-containing gas used in the second reaction zone for the production of alkenyl carboxylate may comprise unreacted molecular oxygen-containing gas from step (a) and/or additional molecular oxygen-containing gas. The additional molecular oxygen-containing gas, if used, may be air or a gas richer or poorer in molecular oxygen than air. A suitable additional molecular oxygen-containing gas may be, for example, oxygen diluted with a suitable diluent, for example nitrogen, argon or carbon dioxide. Preferably, the additional molecular oxygen-containing gas is oxygen. Preferably, at least some of the molecular oxygen-containing gas is fed independently to the second reaction zone from the alkene and carboxylic acid reactants.

The carboxylic acid fed to the second reaction zone for the production of alkenyl carboxylate or alkyl carboxylate may comprise fresh and/or recycle acid. Preferably, at least a portion of the carboxylic acid introduced in to the second reaction zone comprises carboxylic acid produced from the oxidation reaction zone.

The fresh and recycle carboxylic acid may be introduced into the second reaction zone either as separate feed streams or as a single feed stream comprising both fresh and recycle acid.

The carboxylic acid fed to the second reaction zone for the production of alkenyl carboxylate may comprise at least a portion of the acid obtained from downstream processes such as from the separation of the acid from a mixture of the acid/alkenyl carboxylate/water.

At least part of the carboxylic acid fed to the second reaction zone may be liquid.

When solid catalysts are used in the second reaction zone for the production of alkenyl carboxylate, the alkene from the second separation means, the carboxylic acid from the oxidation reaction zone, any additional alkene or carboxylic acid reactants, any recycle streams and molecular oxygen-containing gas are preferably passed through the second reaction zone at a combined gas hourly space velocity (GHSV) of 500–10,000 hr$^{-1}$.

The second reaction zone for the production of alkenyl carboxylate may suitably be operated at a temperature in the range from 140 to 200° C.

The second reaction zone for the production of alkenyl carboxylate may suitably be operated at a pressure in the range 50 to 300 psig.

The second reaction zone for the production of alkenyl carboxylate may suitably be operated as either a fixed or a fluidised bed process.

Carboxylic acid conversions in the range 5 to 80% may be achieved in the second reaction zone for the production of alkenyl carboxylate.

Oxygen conversions in the range 20 to 100% may be achieved in the second reaction zone for the production of alkenyl carboxylate.

Alkene conversions in the range 3 to 100% may be achieved in the second reaction zone for the production of alkenyl carboxylate.

Suitably, the selectivity based on the alkene to the alkenyl carboxylate product, such as vinyl acetate of at least 85%, such as at least 90% may be achieved in the second reaction zone.

In the second reaction zone for the production of alkenyl carboxylate, the catalyst suitably has a productivity in the range 10 to 10000 grams of alkenyl carboxylate per hour per kg of catalyst.

When the alkane used in the process of the present invention is ethane, the product stream from the second reaction zone for the production of alkenyl carboxylate may comprise vinyl acetate, water and acetic acid and optionally also unreacted ethylene, ethane, oxygen, acetaldehyde, nitrogen, argon, carbon monoxide and carbon dioxide. Such a product stream may be separated by azeotropic distillation into an overhead fraction comprising vinyl acetate and water and a base fraction comprising acetic acid and water. The base fraction is removed from the distillation column as liquid from the bottom of the column. Additionally, a vapour from one or more stages above the bottom of the column may also be removed. Prior to such a distillation step, ethylene, ethane, acetaldehyde, carbon monoxide and carbon dioxide, if any, may be removed from the second product stream, suitably as an overhead gaseous fraction from a scrubbing column, in which a liquid fraction comprising vinyl acetate, water and acetic acid is removed from the base. The ethylene and/or ethane may be recycled to the oxidation reaction zone and/or the second reaction zone and/or the second separation means.

Alternatively, at least a portion of the product stream from the second reaction zone is fed together with at least a portion of the carboxylic acid and water fraction obtained from the separation of the product stream from the oxidation reaction zone, to a distillation column for separation of the carboxylic acid from the alkenyl carboxylate and water.

At least a portion of the product stream from the oxidation reaction zone may be co-joined with at least a portion of the product stream from the second reaction zone and the co-joined stream fed, as one or more streams, into the distillation column. Alternatively or additionally, at least a portion of the product stream from the oxidation reaction zone may be fed, as one or more streams, into the distillation column separately from the product stream from the second reaction zone. At least a portion of the product stream from the second reaction zone may be fed, as one or more streams, into the distillation column.

Distillative separation of the product stream from the second reaction zone and the carboxylic acid and water fraction obtained from the separation of the product stream from the oxidation reaction zone produces an overhead fraction comprising alkenyl carboxylate and water and a base fraction comprising carboxylic acid and water.

The alkenyl carboxylate, for example, vinyl acetate is recovered from the overhead fraction, suitably for example by decantation. The recovered alkenyl carboxylate, such as vinyl acetate, may, if desired, be further purified in known manner.

The base fraction comprising carboxylic acid, such as acetic acid and water may be recycled, with or preferably without further purification, to the second reaction zone. Alternatively, the carboxylic acid is recovered from the base fraction and may be further purified if desired, in known manner, for example by distillation.

BRIEF DESCRIPTION OF THE DRAWING

The invention will now be illustrated by reference to the FIGURE.

The FIGURE represents in schematic block-diagram, apparatus suitable for use in the process of the first embodiment of the present invention.

DETAILED DESCRIPTION OF PREFERRED EMBODIMENTS

The apparatus comprises an oxidation reaction zone (1) provided with a supply of ethane and optionally ethylene (3), a supply of a molecular oxygen-containing gas (4), a supply of recycle gas comprising ethane and ethylene (5), a supply (19) of ethane from an ethylene/ethane separation means (21), and an outlet (18) for a first product stream. Depending on the scale of the process, the oxidation reaction zone (1) may comprise either a single reactor or several reactors in parallel or series.

The apparatus also comprises a scrubber (6) for separating the first product stream into a gaseous stream comprising ethylene, ethane and carbon oxides and a liquid stream comprising acetic acid and water. Optionally, the apparatus comprises means (not shown) for removing water from the acetic acid, such as a distillation unit.

The apparatus further comprises a second reaction zone (2) for acetoxylation of ethylene to vinyl acetate which is provided with means (17) for conveying at least a portion of the acetic acid from the scrubber (6) into the second reaction zone, a supply of molecular oxygen-containing gas (9), a supply of recycle acetic acid (10), an optional supply or supplies of acetic acid and/or ethylene (8) and a supply (22) of ethylene from the ethylene/ethane separation means (21). Depending on the scale of the process, the second reaction zone (2) may comprise either a single reactor or several reactors in parallel or in series.

The apparatus comprises a separation means (16) for separating by-products, such as carbon dioxide, from the gaseous stream from scrubber (6) and a separation means (21) for separating at least a portion of the gaseous stream from separation means (16) into an ethylene-rich stream and an ethane-rich stream; a scrubber (12) for the product from the second reaction zone; means (13) for separating acetic acid from the product of the second reaction zone; vinyl acetate purification means (14); optional acetic acid purification means (15) and one or more separation means (16) for separating carbon dioxide from the gaseous stream obtained from scrubber (6) and optionally for recovery of ethylene product.

In use, the oxidation reaction zone (1) is provided with at least one catalyst each active for the oxidation of the ethane to form acetic acid and ethylene. Suitably the oxidation catalysts are solid catalysts. Molecular oxygen-containing gas is fed to the oxidation reaction zone (1) from supply (4) through one or more inlets. A gaseous feedstock comprising ethane and ethylene is fed to the oxidation reaction zone (1) from supply (3). Recycle gas comprising ethane and ethylene is also fed to the oxidation reaction zone (1) from supply (5). Ethane from the ethylene/ethane separation means (21) is fed to the oxidation reaction zone (1) from supply (19).

The molecular oxygen-containing gas, ethane, ethylene and recycle gas are introduced into the oxidation reaction zone (1) through one or more inlets separately or in partial or complete combination. Optionally at least one of the streams fed to the oxidation reactor also comprises water.

In the oxidation reactor a first product stream is produced which comprises ethylene (as product and/or unreacted feed), acetic acid, water, optionally unconsumed molecular oxygen-containing gas, unreacted ethane and by-products such as carbon monoxide, carbon dioxide, inerts and acetaldehyde. At least a portion of this product stream is passed to a scrubber (6) from which a gaseous stream comprising ethylene, ethane and the carbon oxides and a liquid stream comprising acetic acid and water are removed. At least a portion of the gaseous stream is fed, after separating by-products such as carbon dioxide in separation means (16) and optionally recovering a portion of the ethylene product by methods known in the art, to a means (21) for separating the gaseous stream into respective streams rich in ethylene and ethane. At least a portion of a gaseous stream comprising ethylene and ethane from separation means (16) is recycled to the oxidation reaction zone (1) via supply (5). Separation means (21) may comprise at least one cryogenic distillation unit. Alternatively, separation means (21) may comprise a high pressure absorber column and at least one pressure-let down means. The gaseous stream is fed to the absorber column which contains a suitable metallic salt solution such as silver nitrate with which the ethylene is capable of forming a complex. The ethane stream may be removed as an overhead from the column and the ethylene/metal salt complex is removed as a base fraction from the column and passed to the at least one pressure let-down means, such as a flashing valve and drum, in which the complex is decomposed and an ethylene-rich stream is removed as an overhead stream. Optionally, the ethylene stream is then fed to a compressor prior to being fed via supply (22) to the second reaction zone (2). The ethane rich stream from the separation means (21) is fed to the oxidation reaction zone (1) via supply (19).

Acetic acid may be recovered from the liquid stream of scrubber (6), for example by distillation.

At least a portion of the acetic acid from the liquid stream is fed by means (17), optionally via a means for removing water from the liquid stream, into the second reaction zone (2) which is provided with an acetoxylation catalyst, suitably a solid catalyst. A molecular oxygen-containing gas is fed to the second reaction zone from supply (9). Acetic acid is fed to the second reaction zone from recycle supply (10). Optionally, additional ethylene and/or acetic acid may be fed to the second reaction zone from supply or supplies (8). Ethylene is fed from the separation means (21) to the second reaction zone from supply (22). Acetic acid from the liquid scrubber stream, molecular oxygen-containing gas, recycle acetic acid, optional additional supplies of ethylene and/or acetic acid, and ethylene from the separation means (21) are fed into the second reaction zone through one or more inlets separately or in partial or complete combination.

In the second reaction zone the ethylene, acetic acid and molecular oxygen react to produce a second product stream comprising vinyl acetate.

The second reaction product is passed to scrubber (12) from which gas and liquid are separated. Carbon dioxide is separated from the gas and optionally ethylene product recovered, in one or more separation stages (not shown) by methods known in the art. The remaining ethylene and ethane may be recycled to the first and/or second reaction zones. Acetic acid is separated in separation means (13) from the scrubber liquid and is recycled to the second reaction zone via recycle supply (10). Optionally, acetic acid product may be recovered from the recycle stream by means (15), for example by distillation. Vinyl acetate product is recovered from the scrubber liquid by means (14), for example by distillation.

The invention claimed is:

1. A process for the production of an alkyl carboxylate which process comprises the steps:
   (a) contacting in an oxidation reaction zone a $C_2$ to $C_4$ alkane, a molecular oxygen-containing gas, the corresponding alkene and optionally water, in the presence of at least one catalyst active for the oxidation of the alkane to the corresponding alkene and carboxytic acid, to produce a first product stream comprising alkene, unreacted alkane, carboxylic acid and water;
   (b) separating in a first separation means at least a portion of the product stream produced in the oxidation reaction zone into a gaseous stream comprising alkene and unreacted alkane and a liquid stream comprising carboxylic acid and water;
   (c) separating by chemical treatment at least a portion of the gaseous stream obtained from the first separation means into respective streams rich in alkene and alkane; said chemical treatment comprising the steps of:
      (1) contacting the alkene/alkane gaseous stream with a solution of a metal salt capable of selectively chemically absorbing the alkene to produce a chemically absorbed alkene-rich liguid stream, and
      (2) recovering an alkene rich stream from the metal salt solution;
   (d) contacting in a second reaction zone at least a portion of said alkene rich stream obtained from the second separation means and a corresponding carboxylic acid, in the presence of at least one catalyst active for the production of alkyl carboxylate to produce a second product stream comprising alkyl carboxylate.

2. A process for the production of an alkenyl carboxylate which process comprises the steps:
   (a) contacting in an oxidation reaction zone a $C_2$ to $C_4$ alkane, a molecular oxygen-containing gas, the corresponding alkene and optionally water, in the presence of at least one catalyst active for the oxidation of the alkane to the corresponding alkene and carboxylic acid, to produce a first product stream comprising alkene, unreacted alkane, carboxylic acid and water;
   (d) separating in a first separation means at least a portion of the product stream produced in the oxidation reaction zone into a gaseous stream comprising alkene and unreacted alkane and a liquid stream comprising carboxylic acid and water;
   (c) separating by chemical treatment at least a portion of the gaseous stream obtained from the first separation means into respective streams rich in alkene and alkane; said chemical treatment comprising the steps of:
      (1) contacting the alkene/alkane gaseous stream with a solution of a metal salt capable of selectively chemically absorbing the alkene to produce a chemically absorbed alkene-rich liquid stream, and
      (2) recovering an alkene rich stream from the metal salt solution;
   (d) contacting in a second reaction zone at least a portion of said alkene rich stream obtained from the second separation means, a corresponding carboxylic acid and a molecular oxygen-containing gas, in the presence of at least one catalyst active for the production of alkenyl carboxylate to produce a second product stream comprising alkenyl carboxylate.

3. The process according to claim 2, wherein the molecular oxygen-containing gas used in the second reaction zone for the production of alkenyl carboxylate comprises unreacted molecular oxygen-containing gas from step (a) and/or additional molecular oxygen-containing gas.

4. The process according to claim 3, wherein the additional molecular oxygen-containing gas is oxygen.

5. The process according to claim 2, wherein at least some of the molecular oxygen-containing gas is fed independently to the second reaction zone from the alkene and carboxylic acid reactants.

6. The process according to claim 2, wherein at least a portion of the second product stream is fed together with at least a portion of the liquid stream comprising carboxylic acid and water obtained from the first separation means, to a distillation column for separation of the carboxylic acid from the alkenyl carboxylate and water.

7. The process according to claim 2, wherein the C2 to C4 alkane is ethane, the corresponding alkene is ethylene, the corresponding carboxylic acid is acetic acid.

8. The process according to claim 2, wherein the molecular oxygen-containing gas in step (a) is oxygen.

9. The process according to claim 2, wherein the concentration of alkene (as fresh feed and/or recycle component) is from 1 to 50 mol % of the total feed, including recycles, to the oxidation reaction zone.

10. The process according to claim 9, wherein the concentration of alkene is from 1 to 20 mol % of the total feed to the oxidation reaction zone.

11. The process according to claim 2, wherein the concentration of water (as fresh feed and/or recycle component) is from 0 to 50 mol % of the total feed, including recycles, to the oxidation reaction zone.

12. The process according to claim 11, wherein the concentration of water is from 0 to 25 mol % of the total feed to the oxidation reaction zone.

13. The process according to claim 2, wherein the alkene and water are co-fed into the oxidation reaction zone.

14. The process according to claim 2, wherein the alkene and water are used in a ratio of 1:0.1–250 by weight.

15. The process according to claim 2, wherein the first separation means comprises membrane separation, condensation or distillation.

16. The process according to claim 15, wherein the separation is carried out by condensation.

17. The process according to claim 2, wherein the alkene is ethylene and the metal salt capable of selectively chemically absorbing the alkene comprises chromium, copper (I), manganese, nickel, iron, mercury, silver, gold, platinum, palladium, rhodium, ruthenium, osmium, molybdenum, tungsten or rhenium.

18. The process according to claim 17, wherein the metal salt comprises sliver or copper (I).

19. The process according to claim 18, wherein the metal salt is a silver salt.

20. The process according to claim 19, wherein the silver salt is silver nitrate or silver fluoroborate.

21. The process according to claim 20, wherein the metal salt is copper (I) acetate, copper (I) nitrate or copper (I) sulphate.

22. The process according to claim 2, wherein the metal salt solution is aqueous or comprises an organic nitrogen-containing compound.

23. The process according to claim 2, wherein the contacting of the gaseous stream with the metal salt solution is carried out in an absorber column.

24. The process according to claim 2, wherein the alkene-rich stream is recovered from the metal salt solution by heat, reduced pressure or by a combination thereof.

25. The process according to claim 24, wherein the solution is subjected to a reduced pressure such that the metal salt/alkene complex decomposes to release the alkene.

26. The process according to claim 2, wherein, prior to contacting the alkene/alkane gaseous stream with the metal salt solution, the gaseous stream is treated to remove components selected from the group consisting of carbon dioxide, oxygen and oxygenates.

27. The process according to claim 2, wherein the alkane-rich stream obtained from the chemical treatment is fed as one or more streams to the oxidation reaction zone together with additional alkane.

28. The process according to claim 2, wherein the alkene-rich stream is fed as one or more streams to the second reaction zone with optional additional alkene.

29. The process according to claim 28, wherein the additional alkene may be fresh alkene and/or recycled alkene from the second reaction zone and/or a portion of the alkane/alkene stream from the oxidation reaction zone.

30. The process according to claim 2, wherein the concentration of alkene (optional additional alkene feed and alkene obtained from the chemical treatment) fed to the second reaction zone is at least 50 mol % of the total feed to the second reaction zone.

31. The process according to claim 25 wherein the concentration of alkene is least 60 mol % of the total feed to the second reaction zone.

32. The process according to claim 30 wherein the concentration of alkene is up to 85 mol % of the total feed to the second reaction zone.

33. The process according to claim 2, wherein at least a portion of the carboxylic acid introduced in to the second reaction zone comprises carboxylic acid produced from the oxidation reaction zone.

34. The process according to claim 2, wherein at least a portion of the first product stream is co-joined with at least a portion of the second product stream and the co-joined stream fed, as one or more streams, into a distillation column.

35. The process according to claim 2, wherein at least a portion of the first product stream is fed, as one or more streams, into a distillation column separately from the second product stream.

36. A process for the production of vinyl acetate which process comprises the steps:
(a) contacting in an oxidation reaction zone ethane, a molecular oxygen-containing gas, ethylene and optionally water, in the presence of at least one catalyst active for the oxidation of ethane to ethylene and acetic acid, to produce a first product stream comprising ethylene, unreacted ethane, acetic acid and water;
(b) separating in a first separation means at least a portion of the product stream produced in the oxidation reaction zone into a gaseous stream comprising ethylene and unreacted ethane and a liquid stream comprising acetic acid and water;
(c) contacting at least a portion of the gaseous stream obtained from the first separation means with a solution of a metal salt capable of selectively chemically absorbing the ethylene, to produce an ethane rich stream and a chemically absorbed ethylene-rich liquid stream, and recovering said ethylene rich stream from the metal salt solution,
(d) contacting in a second reaction zone at least a portion of said ethylene rich stream recovered in a step (c), acetic acid and a molecular oxygen-containing gas, in the presence of at least one catalyst active for the production of vinyl acetate to produce a second product stream comprising vinyl acetate.

* * * * *